US010550387B2

(12) United States Patent
Kishimoto et al.

(10) Patent No.: US 10,550,387 B2
(45) Date of Patent: Feb. 4, 2020

(54) THERAPEUTIC AGENT FOR A LUNG DISEASE AND/OR METHOD FOR SCREENING FOR THE SAME

(71) Applicants: Tadamitsu Kishimoto, Osaka (JP); Kazuya Masuda, Osaka (JP); CHUGAI SEIYAKU KABUSHIKI KAISHA, Tokyo (JP)

(72) Inventors: Tadamitsu Kishimoto, Osaka (JP); Kazuya Masuda, Osaka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/741,224

(22) PCT Filed: Jun. 30, 2016

(86) PCT No.: PCT/JP2016/069472
§ 371 (c)(1),
(2) Date: Dec. 29, 2017

(87) PCT Pub. No.: WO2017/002928
PCT Pub. Date: Jan. 5, 2017

(65) Prior Publication Data
US 2018/0195064 A1 Jul. 12, 2018

(30) Foreign Application Priority Data
Jun. 30, 2015 (JP) ................. 2015-132230

(51) Int. Cl.
C12N 15/113 (2010.01)
A61P 11/00 (2006.01)
C12Q 1/6851 (2018.01)
C12Q 1/686 (2018.01)

(52) U.S. Cl.
CPC ............ *C12N 15/113* (2013.01); *A61P 11/00* (2018.01); *C12Q 1/686* (2013.01); *C12Q 1/6851* (2013.01); *C12N 2310/14* (2013.01)

(58) Field of Classification Search
None
See application file for complete search history.

(56) References Cited

U.S. PATENT DOCUMENTS

2004/0259247 A1* 12/2004 Tuschl ................ A61K 48/00
435/375

FOREIGN PATENT DOCUMENTS

WO    WO-9604012 A1    2/1996

OTHER PUBLICATIONS

Saito et al. (Arthritis & Rheumatology (May 2014) v. 66(5), pp. 1185-1194) (Year: 2014).*

Global Initiative for Asthma (GINA) Guidelines 2006.
Pauwels, R. A., et al., "Long-Term Treatment With Inhaled Budesonide in Persons With Mild Chronic Obstructive Pulmonary Disease Who Continue Smoking," N Engl J Med 340(25):1948-1953 (1999).
Masuda, K., et al., "Arid5a controls IL-6 mRNA stability, which contributes to elevation of IL-6 level in vivo," PNAS 110(23):9409-9414, with Supporting Information pp. 1-6 (2013).
Saito-Fujita, T., et al., "Attenuated Lung Fibrosis in Interleukin 6 Knock-out Mice after C-ion Irradiation to Lung," J Radiat Res 52:270-277 (2011).
Masuda, K., et al., "ARID5a is an IL-6 mRNA stability protein. Chlorpromazine mediates its inhibitory effect on IL-6 production in macrophages through inhibition of ARID5A expression," Cytokine 59(3):544, P079 (2012).
Tabata, C., et al., "Development Research of Novel Agents for the Treatment of Interstitial Pneumonia/Pulmonary Fibrosis," Acta Med Hyogo 37(1):73-78, with English translation (2012).
Chen, C.-Y., et al., "Luteolin Ameliorates Experimental Lung Fibrosis Both *in Vivo* and *in Vitro*: Implications for Therapy of Lung Fibrosis," J Agric Food Chem 58:11653-11661 (2010).
Dubey, K. P., et al., "A role of Arid5a in bleomycin-induced lung injury," Proceedings of the Japanese Society for Immunology, 44:88, Proceedings 1-I-W16-14-P (2015).
International Search Report for International Application No. PCT/JP2016/069472 dated Aug. 9, 2016, 2 pages.
Saito, Y., et al., "AT-Rich-Interactive Domain-Containing Protein 5A Functions as a Negative Regulator of Retinoic Acid Receptor-Related Orphan Nuclear Receptor γt-Induced Th17 Cell Differentiation," Arthritis & Rheumatology 66(5):1185-1194 (2014).
Vadas, P., et al., "Potential therapeutic efficacy of inhibitors of human phospholipase $A_2$ in septic shock," Agents and Actions 19(3/4):194-202 (1986).
Masuda, K., et al., "ARID5a is an IL-6 mRNA stability protein. Chlopromazine mediates its inhibitory effect on IL-6 production in macrophages through inhibition of ARID5A expression," Abstract P079, Cytokine 59(3):544 (2012).
Masuda, K., et al., "Arid5a contributes to stabilization of IL-6 mRNA, and elevation of IL-6 level in vivo," Abstract 176, Cytokine 63:284 (2013).
Ramachandran, G., "Gram-positive and gram-negative bacterial toxins in sepsis," Virulence 5(1):213-218 (2013).
Extended European Search Report dated Jul. 27, 2018 in European Patent Application No. 15873058.0, 12 pages.
De Souza, A. T., et al., "Transcriptional and phenotypic comparisons of *Ppara* knockout and siRNA knockdown mice," Nucleic Acids Research 34(16):4486-4494 (2006).
Amano, K., et al., "Arid5a cooperates with Sox9 to stimulate chondrocyte-specific transcription," Mol Biol Cell 22:1300-1311 (2011).
Vyas, D., et al., "Early antibiotic administration but not antibody therapy directed against IL-6 improves survival in septic mice predicted to die on basis of high IL-6 levels," *Am J Physiol Regul Integr Comp Physiol*, 289: R1048-R1053, (2005).

(Continued)

*Primary Examiner* — J. E Angell
(74) *Attorney, Agent, or Firm* — Nixon & Vanderhye P.C.

(57) ABSTRACT

Provided are a therapeutic and/or prophylactic agent for a lung disease and a method for screening for the therapeutic and/or prophylactic agent. Provided are a therapeutic and/or prophylactic agent for a lung disease comprising an Arid5A inhibitor as an active ingredient and a method for screening for the therapeutic and/or prophylactic agent.

9 Claims, 6 Drawing Sheets
Specification includes a Sequence Listing.

(56) References Cited

OTHER PUBLICATIONS

Lv, S., et al., "Anti-TNF-α therapy for patients with sepsis: a systematic meta-analysis," *Int J Clin Pract*, 68(4): 520-528, (Apr. 2014).

Tarazona, R., et al., "Chlorpromazine Amplifies Macrophase-Dependent IL-10 Production In Vivo," *J Immunol*, 154: 861-870 (1995).

Osaka University Saishin Joho (online), "A key to revealing the mechanism of the development of incurable immune diseases—Discovery of molecules related to an abnormal production of IL-6," URL<http://www.osaka-u.ac.jp/ja/news/ResearchRelease/2013/05/20130514_1> [retrieval date Mar. 3, 2016] (May 14, 2013), and an English translation thereof.

Takamura, S. (Akashi), "Endotoxin shock and TLR—A mechanism of recognizing endotoxin by TLR," *Inflammation and Immunology*, 13(1): 37-44, (2005), and an English translation thereof.

Greenhill, C. J., et al., "IL-6 *Trans*-Signaling Modulates TLR4-Dependent Inflammatory Responses via STAT3," *J Immunol*, 186: 1199-1208, (2011).

Riedemann, N. C., et al., "Protective Effects of IL-6 Blockade in Sepsis Are Linked to Reduced C5a Receptor Expression," *J Immunol*, 170: 503-507, (2003).

Mahabub-UZ, Z. M., et al., "Pathogenic roles of Arid5a in endotoxin shock," *Proceedings of the Japanese Society for Immunology*, 44: 192, 3-G-W44-8-P, (Oct. 30, 2015).

\* cited by examiner

Arid5a⁻/⁻

WT

Arid5a⁻/⁻

WT

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: primer1

<400> SEQUENCE: 1
atactttctc ggcaggagca                                          20

<210> SEQ ID NO 2
<211> LENGTH: 20
<212> TYPE: DNA
<213> ORGANISM: Artificial Sequence
<220> FEATURE:
<223> OTHER INFORMATION: primer2

<400> SEQUENCE: 2
tgaatgaact gcaggacgag                                          20
```

US 10,550,387 B2

THERAPEUTIC AGENT FOR A LUNG DISEASE AND/OR METHOD FOR SCREENING FOR THE SAME

CROSS-REFERENCE TO RELATED APPLICATIONS

This application is a U.S. National Phase of PCT Application No. PCT/JP2016/069472, filed Jun. 30, 2016, which claims the benefit of Japanese Patent Application No. 2015-132230, filed Jun. 30, 2015, each of which is incorporated herein by reference in its entirety.

REFERENCE TO SEQUENCE LISTING SUBMITTED ELECTRONICALLY

The content of the electronically submitted sequence listing (Name: 6663_0051_Sequence_Listing.txt; Size: 644 bytes; and Date of Creation: Dec. 20, 2017) filed with the application is incorporated herein by reference in its entirety.

TECHNICAL FIELD

The present invention relates to a novel therapeutic agent for a lung disease and/or a method for screening for the novel therapeutic agent.

BACKGROUND ART

Lung diseases include many known inflammatory lung diseases such as acute bronchitis due to acute inflammation caused by viruses, bacteria, or the like; chronic bronchial asthma mainly developed from respiratory tract inflammation due to eosinophils; interstitial pneumonia involving lung structure damage caused by alveolar epithelial inflammation; and chronic obstructive pulmonary disease (COPD), which is known as a disease characterized by chronic pulmonary inflammation caused by various factors, especially smoking, leading to alveolar wall destruction and bronchial mucous gland hypertrophy and the like resulting in shortness of breath, increased cough and sputum, etc.

In the pathological process of the inflammatory lung diseases as described above, it has been known that transmitters, called chemotactic factors, released at early stage will stimulate inflammatory cells, such as neutrophils, basophils, eosinophils, and macrophages and the like, to migrate to local sites and the migrated inflammatory cells will release injurious enzymes and radicals to damage tissues and at the same time will release cytokine or the like, resulting in further migration and activation of the inflammatory cells. When such inflammation develops in respiratory tracts, the infiltrating inflammatory cells will damage bronchial and pulmonary tissues. This finally leads to impairment of respiratory function, including reduction in respiratory flow and oxygen exchange capacity, characteristic of each of the diseases. Lung structure and function are further markedly suppressed, and many cases may progress to intractable diseases that will eventually lead to fibrogenesis or honeycomb lung.

Such inflammatory lung diseases have been treated with drugs with anti-inflammatory effects, and mild to moderate bronchial asthma has been known to completely response to adrenocortical steroids (see Non Patent Literature 1). Interstitial pneumonia has been also treated with adrenocortical steroids at acute exacerbation and combined with immunosuppressive agents where appropriate. Further progression will certainly induce hypoxemia and therefore require oxygen therapy including home oxygen therapy. Adrenocortical steroids have been reported to prevent exacerbation of COPD but their effects on the pathology of COPD are limited (see Non Patent Literature 2). Pulmonary fibrosis has been also treated with steroid therapy although lesions often remain and acute exacerbations are frequently observed due to side effects or reduction or withdrawal of steroidal agents. This is never satisfying in clinical cure and therefore there are needs to develop novel therapeutic agents.

AT Rich Interactive Domain 5A (hereinafter abbreviated as Arid5A) has been reported to be a protein that stabilizes IL-6 mRNA (see, e.g., Non Patent Literature 3).

CITATION LIST

Non Patent Literature

Non Patent Literature 1: GINA Guideline, 2006
Non Patent Literature 2: N. Engl. J. Med., 1999, 340 (25), 1948-1953
Non Patent Literature 3: PNAS, 110, 23, 9404-9414 (2013)

SUMMARY OF INVENTION

Technical Problem

However, the relationship between Arid5A and a lung disease has been unknown.

The present invention intends to provide a more effective therapeutic agent for a lung disease and a method for screening for the therapeutic agent.

Solution to Problem

The present invention specifically includes the following:
[1] A therapeutic agent and/or prophylactic agent for a lung disease, comprising an Arid5A inhibitor as an active ingredient.
[2] The therapeutic agent and/or prophylactic agent for a lung disease according to [1], wherein the Arid5A inhibitor is at least one substance selected from the group consisting of a nucleic acid oligo and an Arid5A antibody.
[3] The therapeutic agent and/or prophylactic agent for a lung disease according to [2], wherein the nucleic acid oligo is an oligo consisting of a natural or non-natural RNA or DNA.
[4] The therapeutic and/or prophylactic agent for a lung disease according to any of [1] to [3], wherein the lung disease is pulmonary fibrosis.
[5] A method for screening for a candidate substance useful for the treatment and/or prevention of a lung disease, wherein the method comprises:
  (a) detecting an effect of test agents on the expression of Arid5A and
  (b) selecting the agents that decrease the expression of Arid5A as compared to the absence of the test agents.
[6] A method for screening for a candidate substance useful for the treatment and/or prevention of a lung disease, wherein the method comprises:
  (a) administering test agents to experimental animals,
  (b) determining an effect on the expression of Arid5A by PCR, and
  (c) selecting the agents that decrease the expression of Arid5A as compared to no administration of the test agents to the experimental animals.

[7] A method for screening for a candidate substance useful for the treatment and/or prevention of a lung disease, wherein the method comprises:
(a) detecting an effect of test agents on the function of Arid5A and
(b) selecting the agents that decrease the function of Arid5A as compared to the absence of the test agents.
[8] The method for screening for a candidate substance useful for the treatment and/or prevention of a lung disease according to [7], wherein the function of Arid5A is to stabilize IL-6 mRNA.
[9] The method for screening according to any of [5] to [8], wherein the lung disease is pulmonary fibrosis.
[10] A method for the treatment and/or prevention of a lung disease, comprising administering an Arid5A inhibitor.
[11] An Arid5A inhibitor for use in the treatment and/or prevention of a lung disease.
[12] Use of an Arid5A inhibitor for production of a therapeutic and/or prophylactic agent for a lung disease.

Advantageous Effects of Invention

The therapeutic agent for a lung disease according to the present invention has high therapeutic efficacy for a lung disease. The present invention also provides a method for screening for a therapeutic agent with high therapeutic efficacy.

BRIEF DESCRIPTION OF DRAWINGS

FIG. 1A, top: the wild type allele of Arid5A, middle: the targeting vector, and bottom: the expected mutated allele. The main part of DNA binding domain is substituted with Neo-cassette interrupted by loxp sequences at both ends of the Neo-cassette. FIG. 1B, genotyping by Southern blotting analysis; wild type (+/+), heterozygote (+/−).

DESCRIPTION OF EMBODIMENTS

Figure 1A:
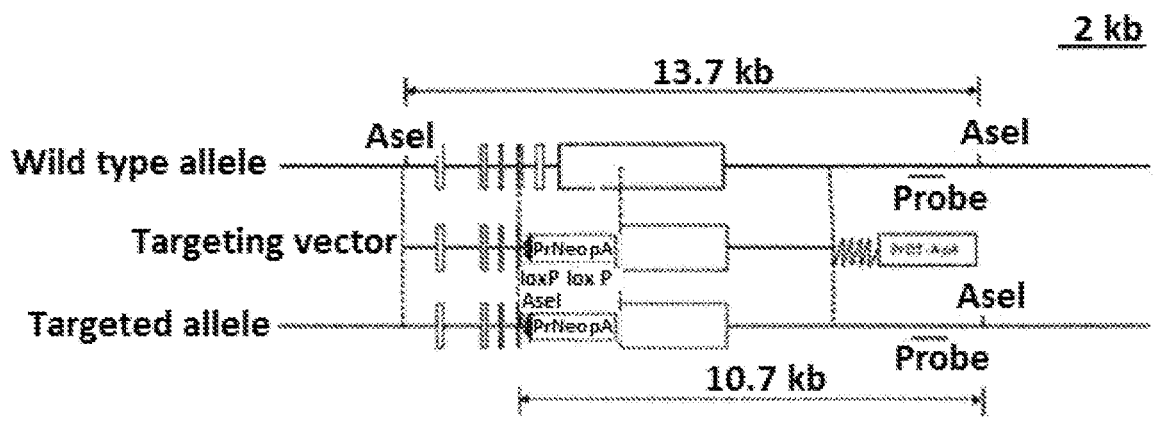
FIGS. 1A and 1B show the generation of Arid5A-deficient mice.

The present invention will be now described in more detail below.

The present invention relates to a therapeutic agent for a lung disease and a method for screening for the therapeutic agent.

"Arid5A" in the present invention refers to AT Rich Interactive Domain 5A (hereinafter abbreviated as Arid5A) and has been reported to be a protein that stabilizes IL-6 mRNA. For example, human Arid5A includes various isoforms (NCBI accession numbers NP997646.1, XP006712266.1, XP006712265.1, XP005263918.1, XP005263913.1, XP005263917.1, etc.). Similarly, mouse Arid5A also includes various isoforms (NCBI accession numbers NP00165676.1, NP00165677.1, NP001277655.1, NP001277656.1, NP666108.2, etc.).

"Arid5A inhibitor" in the present invention refers to a substance that inhibits the expression and/or function of Arid5A. The Arid5A inhibitor may be a substance that directly inhibits the expression itself of Arid5A or may be a substance that indirectly inhibits a biological function of Arid5A by binding to a molecule affected by Arid5A (e.g., IL-6 mRNA). The Arid5A inhibitor preferably includes a substance that inhibits stabilization of IL-6 mRNA by binding competitively with Arid5A to IL-6 mRNA. For example, human IL-6 mRNA includes various isoforms (NCBI accession numbers NM000600.3, XM005249745.2, etc.). Similarly, mouse IL-6 mRNA also includes various isoforms (NCBI accession number NM031168.1, etc.).

The Arid5A inhibitor according to the present invention includes, but is not particularly limited to, for example, low-molecular substances such as an anti-Arid5A antibody, a nucleic acid oligo, and chlorpromazine. Preferred examples of the Arid5A inhibitor according to the present invention include an siRNA.

Arid5A expression can be inhibited, for example, by utilizing RNA interference effect on the expression of Arid5A gene. RNA interference is a method that has been reported to suppress gene expression using RNA (Genes and Development, 16, 948-958 (2002)) and is a phenomenon in which the expression of both a transduced foreign gene and an endogenous target gene is suppressed by transducing a duplex RNA having a sequence identical or similar to the sequence of target gene into cells. Specifically, an siRNA or an antisense nucleic acid having an RNA interference effect on the expression of Arid5A gene can be used to inhibit the expression of Arid5A gene.

"Nucleic acid oligo" according to the present invention means a nucleic acid oligomer that controls the function of Arid5A gene or protein and includes an siRNA, an shRNA, an antisense nucleic acid, a decoy nucleic acid, and a nucleic acid aptamer.

The nucleic acid oligo according to the present invention can include preferably an siRNA or an shRNA. The siRNA means a duplex RNA consisting of a short strand having a length sufficient to avoid toxicity in cells and can have, for example, 15 to 49 base pairs, suitably 15 to 35 base pairs, and more suitably 21 to 30 base pairs. The shRNA is another type of RNA in which a single-stranded RNA forms a duplex by adopting a hairpin structure.

The siRNA and shRNA are not required to be completely identical to the target gene, but have a sequence homology of at least 70% or more, preferably 80% or more, more preferably 90% or more, and most preferably 95% or more.

A duplex region, in which base pairing occurs, in an siRNA and shRNA may include not only a region that has perfect pairing of bases but also a region that has mispairing of bases due to mismatch (in which corresponding bases are not complementary), bulge (in which either strand has no corresponding base), and the like. In the present invention, a region of duplex RNA, in which base pairing occurs, in a dsRNA may comprise both bulge and mismatch.

"Antisense nucleic acid" in the present invention is an antisense nucleic acid complementary to the product transcribed from DNA encoding Arid5A. Effects of the target gene expression suppressed by an antisense nucleic acid are caused by multiple factors as listed below. The factors include degradation due to activity of an RNase that recognizes RNA duplex, inhibition of transcriptional initiation due to triplex formation, suppression of transcription due to hybridization with a site having an open-loop structure locally formed by RNA polymerase, inhibition of transcription due to hybridization with RNA that is in the process of being synthesized, suppression of splicing due to hybridization at the junction between the intron and exon, suppression of splicing due to hybridization with a spliceosome-forming site, suppression of translocation from nucleus to cytoplasm due to hybridization with mRNA, suppression of translation due to hybridization with a translation initiation factor binding site, blocking of peptide chain elongation due to hybridization with a coding region or polysome binding site of mRNA, and suppression of gene expression due to hybridization with a site of interaction between nucleic acid and protein. The expression of target gene can be suppressed by inhibiting the process of transcription, splicing, or translation among others.

The antisense sequences used in the present invention may suppress the expression of target gene with any effect as described above. In one aspect, design of an antisense sequence complementary to a noncoding region near 5' end of Arid5A mRNA should be effective in the inhibition of gene translation. However, sequences complementary to a coding region or the 3' noncoding region may be also used. Thus, sequences complementary to not only a coding region but also a noncoding region of gene can be used. Hence, the antisense nucleic acids used in the present invention also include nucleic acids comprising antisense sequences against not only coding regions but also noncoding regions of the gene. The antisense nucleic acids have complementarity to the transcriptional products of the target gene of preferably 90% or more and most preferably 95% or more. The length of antisense RNAs that effectively inhibit the expression of target gene using the antisense sequences is not particularly limited.

"Decoy nucleic acid" in the present invention is a nucleic acid oligo having homology to the sequence of IL-6 mRNA recognized by Arid5A. The decoy nucleic acid binds Arid5A instead of the sequence of IL-6 mRNA and inhibits Arid5A function.

"Anti-Arid5A antibody" in the present invention can be obtained as a polyclonal antibody or a monoclonal antibody using any known means. The antibody used in the present invention is derived from any source, which is not particularly limited, and can include an antibody preferably derived from mammals and more preferably derived from human. Monoclonal antibodies derived from mammals include an antibody produced by a hybridoma and an antibody produced by a host transformed with an expression vector comprising an antibody gene using a genetic engineering technique. The antibodies inhibit the functional expression of Arid5A by binding Arid5A.

Antibody-producing hybridomas can be produced essentially by using known techniques as described below. More specifically, Arid5A is used as a sensitizing antigen for immunization according to a conventional immunization method. The resulting immune cells are fused with known parent cells according to a conventional cell fusion method.

The fused cells are screened for a monoclonal antibody-producing cell according to a conventional screening method.

Specifically, an anti-Arid5A antibody may be produced as follows. For example, human Arid5A used as an antigen for obtaining the antibody can be obtained using Arid5A gene/amino acid sequence disclosed in known literatures.

The sequence of Arid5A gene is inserted into any known expression vector system. The resulting expression vector system is used to transform suitable host cells. Arid5A protein of interest is then purified from the host cells or from the culture supernatant of the host cells using any known method. The purified Arid5A protein may be used as a sensitizing antigen. Arid5A protein produced by chemical synthesis may be also used as a sensitizing antigen. A fusion protein between Arid5A protein and any other protein may be also used as a sensitizing antigen.

Mammals immunized with the sensitizing antigen are not particularly limited, but are preferably selected in consideration of compatibility with parent cells used in cell fusion. Typically, rodents such as mouse, rat, and hamster are used.

Immunization of an animal with the sensitizing antigen is performed according to any known method. For example, the immunization is generally performed by intraperitoneally or subcutaneously injecting the sensitizing antigen into a mammal. Specifically, the sensitizing antigen is diluted with Phosphate-Buffered Saline (PBS), physiological saline, or the like to provide a suitable amount of suspension. The suspension is optionally mixed with a conventional adjuvant, such as complete Freund's adjuvant, in a suitable amount and then emulsified. The emulsified product is preferably administered to a mammal in some doses every 4 to 21 days. Suitable carriers can be also used in the immunization of the sensitizing antigen.

After the immunization and confirmation of increase in the level of the desired antibody in serum, immune cells are removed from the mammal and are submitted to cell fusion. Preferred immune cells submitted to cell fusion include particularly splenic cells.

The immune cells are fused with other parent cells. The other parent cells appropriately used include mammalian myeloma cells including a variety of known cell lines such as P3X63Ag8.653 (J. Immunol. 123, 1548-1550 (1979)).

Cell fusion between the immune cells and myeloma cells can be performed essentially using any known method, for example, according to the method of Milstein et al. (Methods Enzymol., 73, 3-46 (1981)).

More specifically, the cell fusion is performed, for example, in a standard nutrient medium in the presence of a cell fusion-promoting agent. The cell fusion-promoting agent that may be used includes, for example, polyethylene glycol (PEG) and Sendai virus (HVJ). In addition, to increase fusion efficiency, auxiliary agents such as dimethyl sulfoxide can be added and used as desired.

The immune cells and myeloma cells are preferably used, for example, as a ratio in which the number of immune cells is 1- to 10-times more than the number of myeloma cells. Culture media that can be used in the cell fusion include, for example, RPMI1640 medium and MEM medium, which both are suitable for proliferation of the myeloma cell line, and other conventional culture media used in this type of cell culture. Moreover, a serum complement such as fetal calf serum (FCS) can be also used.

In the cell fusion, a given amount of the immune cells and myeloma cells are mixed thoroughly in the culture medium. Then, a PEG solution preheated to about 37° C., in which the PEG solution has, for example, an average molecular weight of about 1,000 to 6,000, is typically added in a concentration of 30 to 60% (w/v) and mixed to form fusion cells of interest (hybridomas). Subsequently, to remove cell fusing agents and other agents unfavorable for the growth of the hybridomas, the following steps can be sequentially repeated: adding a suitable culture medium, centrifuging the resulting suspension, and removing the supernatant.

The hybridomas are selected by culturing the hybridomas in a conventional selective culture medium, such as HAT culture medium (a culture medium containing hypoxanthine, aminopterin, and thymidine). The culture in HAT culture medium is continued for a period of time sufficient to kill any cells (non-fused cells) other than the hybridomas of interest, usually for a few days to weeks. The hybridomas producing the antibody of interest are then screened for and cloned using a conventional limiting dilution method.

The desired human antibody having the binding activity to the desired antigen or antigen-expressing cells can be obtained not only from the hybridomas by immunizing a nonhuman animal with the antigen but also by sensitizing human lymphocytes to the desired antigenic protein or the cells expressing the antigen in vitro and fusing the sensitized B lymphocytes with human myeloma cells, e.g., U266 (see Japanese Patent Publication No. 1-59878). Moreover, the desired human antibody may be obtained by administering the antigen or the cells expressing the antigen to a transgenic animal having human antibody gene repertoires according to the method described above (see International Publication No. WO 93/12227, etc.).

The generated hybridomas producing a monoclonal antibody can be subcultured in a conventional culture medium and stored in liquid nitrogen over a long period of time.

A method for obtaining monoclonal antibodies from the hybridomas embraces a method of culturing the hybridomas according to any conventional method and collecting the culture supernatant to obtain the monoclonal antibodies or a method of administering the hybridomas to a mammal compatible with the hybridomas, allowing the hybridomas to be proliferated, and collecting the peritoneal fluid to obtain the monoclonal antibodies. The former method is suitable for obtaining highly-pure antibodies while the latter method is suitable for high volume production of antibodies.

The monoclonal antibodies used in the present invention may be recombinant antibodies, which are produced by a gene recombination technique, which technique comprises cloning an antibody gene from a hybridoma, inserting the gene into a suitable vector, and transducing the vector into a host (see, e.g., Borrebaeck C. A. K. and Larrick J. W. THERAPEUTIC MONOCLONAL ANTIBODIES, Published in the United Kingdom by MACMILLAN PUBLISHERS LTD, 1990).

Specifically, mRNA encoding the variable (V) region of the antibody of interest is isolated from cells producing the antibody, for example, hybridomas. The mRNA is isolated by preparing total RNA using any known method, such as guanidine ultracentrifugation (Chirgwin, J. M. et al., Biochemistry (1979) 18, 5294-5299) and the AGPC method (Anal. Biochem. (1987) 162, 156-159), to prepare mRNA, for example, using mRNA Purification Kit (from Pharmacia). Alternatively, mRNA can be directly prepared by using QuickPrep mRNA Purification Kit (from Pharmacia).

The obtained mRNA is used with a reverse transcriptase to synthesize cDNA of the V region of antibody. The cDNA can be synthesized by using AMV Reverse Transcriptase First-strand cDNA Synthesis Kit and the like. The cDNA can be also synthesized and amplified using 5'-RACE (Frohman, M. A. et al., Proc. Natl. Acad. Sci. USA (1988) 85, 8998-9002; Belyaysky, A. et. al., Nucleic Acid Res. (1989) 17, 2919-2932) with 5'-Ampli FINDER RACE Kit (from Clontech) and PCR. The resulting PCR products are purified to obtain the DNA fragment of interest, and the fragment is linked to a vector DNA. Furthermore, the desired recombinant vector is prepared by using the linked vector DNA to make a recombinant vector, transducing the recombinant vector into *Escherichia coli* cells or the like, and selecting colonies. The base sequence of the DNA of interest is confirmed using any known method, for example, the deoxy method.

Once the DNA encoding the V region of the antibody of interest is obtained, this DNA is linked to a DNA encoding the desired constant region (C region) of antibody and the linked DNA is inserted into an expression vector. Alternatively, the DNA encoding the V region of antibody may be inserted into an expression vector comprising the DNA of the C region of antibody.

For production of the antibody used in the present invention, an antibody gene is inserted into an expression vector to allow the antibody gene to be expressed under the control of an expression regulatory region, such as enhancer and promoter, as described below. The expression vector is then transformed into host cells to permit expression of the antibody.

Gene recombinant antibodies that have been artificially modified for decreasing xenogeneic antigenicity against human and the like can be used in the present invention. The gene recombinant antibodies include, for example, chimeric antibodies, humanized antibodies, and human antibodies. These modified antibodies can be produced using any known method.

Chimeric antibodies are obtained by linking the DNA encoding the V region of antibody obtained as described above to the DNA encoding the C region of human antibody, inserting the linked DNA into an expression vector, transducing the expression vector into a host, and allowing the host to produce the chimeric antibodies (see European Patent Application Publication No. EP125023, International Publication No. WO 92-19759). This known procedure can be used to obtain the chimeric antibodies useful for the present invention.

Humanized antibodies, also referred to as reshaped human antibodies or human-typed antibodies, are antibodies in which complementarity-determining region (CDR) of antibody from a nonhuman mammal, such as mouse, is grafted into the complementarity-determining region of a human antibody. The general gene recombination techniques for producing humanized antibodies are known (see European Patent Application Publication No. EP125023, International Publication No. WO 92-19759).

Specifically, a DNA sequence that is designed to link CDRs of a mouse antibody to framework regions (FRs) of a human antibody is synthesized using PCR with some oligonucleotides produced to have overlapping sequences in the terminal parts of the oligonucleotides. The resulting DNA is linked to the DNA encoding the C region of a human antibody, and then inserted into an expression vector. The expression vector is transduced into a host to result in production of the antibody (see European Patent Application Publication No. EP239400, International Publication No. WO 92-19759).

The FRs of a human antibody linked to the CDRs are selected to allow the complementarity-determining regions to form a functional antigen binding site. One or more amino acids in the framework region of the variable region of an antibody may be optionally substituted to allow complementarity-determining regions of a reshaped human antibody to form a functional antigen binding site as required (Sato, K. et al., Cancer Res. (1993) 53, 851-856).

Chimeric antibodies and humanized antibodies have C regions of human antibodies. The C regions of human antibodies include Cγ. For example, Cγ1, Cγ2, Cγ3, or Cγ4 can be used. The C regions of human antibodies may be also modified for improving stability of the antibody or production of the antibody.

Chimeric antibodies consist of variable regions of antibodies from nonhuman mammals and C regions of human antibodies. Humanized antibodies consist of complementarity-determining regions of antibodies from nonhuman mammals and framework regions and C regions of human antibodies. Both chimeric antibodies and humanized antibodies have low antigenicity in human bodies and therefore are useful for antibodies used in the present invention.

The methods known to provide human antibodies include, in addition to the methods as described previously, a technique of obtaining human antibodies by the panning of a human antibody library. For example, a variable region of human antibodies can be expressed in the form of single-chain antibody (scFv) on the surface of phages by phage display, and the phages that bind an antigen of interest can be selected. The selected phages are analyzed for the genes by sequencing the DNA encoding variable regions of the human antibodies that bind the antigen of interest. Once the DNA sequences of scFvs that bind the antigen are determined, expression vectors suitable for the sequences can be made. The expression vectors can be used to obtain human antibodies. These methods are well known and are described in WO 92/01047, WO 92/20791, WO 93/06213, WO 93/11236, WO 93/19172, WO 95/01438, and WO 95/15388, which can be referenced.

The antibody gene constructed as described above can be expressed using any known method, obtaining the antibody. For mammalian cells, the antibody can be expressed using a DNA that is obtained by operably linking a useful promoter usually used, the antibody gene to be expressed, and a poly A signal downstream of the 3' end of the antibody gene, or a vector comprising the DNA. Promoters/enhancers can include, for example, human cytomegalovirus immediate early promoter/enhancer.

Other promoters/enhancers that can be used for antibody expression in the present invention include a promoter/enhancer of viruses such as retrovirus, polyomavirus, adenovirus, and simian virus 40 (SV40), and a promoter enhancer from mammalian cells such as human elongation factor 1α (HEF1α).

For example, the SV40 promoter/enhancer can be easily used according to the method of Mulligan et al. (Mulligan, R. C. et al., Nature (1979) 277, 108-114), and the HEF1α promoter/enhancer can be easily used according to the method of Mizushima et al. (Mizushima, S. and Nagata, S. Nucleic Acids Res. (1990) 18, 5322).

For *Escherichia coli*, the antibody can be expressed by operably linking a useful promoter usually used, a signal sequence for antibody secretion, and the antibody gene to be expressed. The promoter can include, for example, lacZ promoter and araB promoter. The lacZ promoter may be used according to the method of Ward et al. (Ward, E. S. et al., Nature (1989) 341, 544-546; Ward, E. S. et al., FASEB J. (1992) 6, 2422-2427), and the araB promoter may be used according to the method of Better et al. (Better, M. et al., Science (1988) 240, 1041-1043).

The signal sequence for antibody secretion that is used for production in the periplasm of *Escherichia coli* may be pelB signal sequence (Lei, S. P. et al., J. Bacteriol. (1987) 169, 4379-4383). The antibody produced in the periplasm is separated followed by appropriate refolding of the structure of the antibody (see, e.g., WO 96/30394).

Origins of replication that can be used include those derived from SV40, polyomavirus, adenovirus, bovine papillomavirus (BPV), and the like. Moreover, the expression vectors can comprise, as a selection marker, aminoglycoside phosphotransferase (APH) gene, thymidine kinase (TK) gene, *Escherichia coli* xanthine-guanine phosphoribosyltransferase (Ecogpt) gene, dihydrofolate reductase (dhfr) gene, and the like, for amplifying the gene copy number in host cell systems.

Any production system may be used for producing the antibodies used in the present invention. The production system for antibody production includes in vitro and in vivo production systems. The in vitro production system includes a production system using eukaryotic or prokaryotic cells.

The production system using eukaryotic cells includes a production system using animal, plant, or fungal cells. The animal cells known to be used include (1) mammalian cells, such as, CHO, COS, myeloma, baby hamster kidney (BHK), Hela, and Vero, (2) amphibian cells, such as Xenopus oocyte, and (3) insect cells, such as sf9, sf21, and Tn5. The plant cells known to be used include cells from *Nicotiana tabacum*, which may be used for callus culture. The fungal cells known to be used include yeasts, such as genus *Saccharomyces* including *Saccharomyces cerevisiae*, and filamentous bacteria, such as genus *Aspergillus* including *Aspergillus niger*.

The production system using prokaryotic cells includes a production system using bacterial cells. The bacterial cells known to be used include *Escherichia coli* (*E. coli*) and *Bacillus subtilis*.

These cells are transformed with an antibody gene of interest, and the transformed cells can be cultured in vitro to obtain the antibody. The culture is performed according to any known method. For example, culture media that can be used include DMEM, MEM, RPMI1640, and IMDM. A serum complement such as fetal calf serum (FCS) can be also used. The cells transduced with the antibody gene may be also injected into peritoneal cavity in animals to produce the antibody in vivo.

On the other hand, the in vivo production system includes a production system using animals and plants. The production system using animals includes a production system using mammals or insects.

The mammals that can be used include goat, pig, sheep, mouse, and cattle (Vicki Glaserm, SPECTRUM Biotechnology Applications, 1993). The insects that can be used include silkworm. The plants that can be used include, for example, tobacco.

The antibody is produced in the animals or plants into which the antibody gene has been transduced, and collected. For example, the antibody gene is interrupted by a gene encoding a protein specifically produced in milk, such as goat β casein, to prepare a fusion gene. The DNA fragments comprising the fusion gene with the antibody gene are transferred into goat embryos. The embryos are implanted into female goats. The desired antibody is obtained from milk produced by the goats received the embryos, which are transgenic goats, or their offspring. In order to increase the amount of milk comprising the desired antibody produced by the transgenic goats, any suitable hormone may be administered to the transgenic goats (Ebert, K. M. et al., Bio/Technology (1994) 12,699-702).

Silkworms are also used to obtain the desired antibody by infecting the silkworms with a baculovirus having the antibody gene of interest inserted and collecting the fluid of the infected silkworms (Maeda, S. et al., Nature (1985) 315, 592-594). In addition, when tobacco is used, the antibody gene of interest is inserted into a plant expression vector, such as pMON530, and the vector is transduced into a bacterium such as *Agrobacterium tumefaciens*. The bacterium is used to infect tobacco such as *Nicotiana tabacum*, and the desired antibody is obtained from leaves of the tobacco (Julian, K.-C. Ma et al., Eur. J. Immunol. (1994) 24, 131-138).

When an antibody is produced in the in vitro or in vivo production system as described above, host cells may be co-transformed with expression vectors into which a DNA encoding the heavy chain (H chain) or light chain (L chain) of the antibody is separately inserted or may be transformed with a single expression vector into which DNAs encoding H chain and L chain are inserted (see International Publication No. WO 94-11523).

The antibodies produced and expressed as described above can be separated from intracellular or extracellular components or hosts and purified to homogeneity. The antibodies used in the present invention can be separated and purified by affinity chromatography. Columns used in affinity chromatography include, for example, protein A columns and protein G columns. Carriers for protein A columns include, for example, Hyper D, POROS, and Sepharose F.F. Other details are not limited at all as long as the details are used for a method for separating and purifying usual proteins.

For example, the antibody used in the present invention can be separated and purified by appropriately selecting or combining a chromatography except the affinity chromatography as described above, a filter, ultrafiltration, salt precipitation, dialysis, and the like. The chromatography includes, for example, ion exchange chromatography, hydrophobic chromatography, and gel filtration. These chromatographies are applicable to high performance liquid chromatography (HPLC). Reverse phase HPLC may be also used.

The concentration of the antibody obtained above can be measured by determination of absorbance, ELISA, or the like. More specifically, in the determination of absorbance, the antibody is suitably diluted with PBS (−) followed by determination of absorbance at 280 nm to calculate the concentration of the antibody by setting the absorbance at the concentration of 1 mg/ml to 1.350 D. In ELISA, the concentration of the antibody can be measured as follows. One hundred µl of goat anti-human IgG (from TAG) diluted to 1 µg/ml with 0.1 M bicarbonate buffer (pH 9.6) is added to a 96-well plate (from Nunc) and incubated at 4° C. overnight to immobilize the antibody. After blocking, 100 µl of the antibody used in the present invention or a sample containing the antibody that is suitably diluted, or human IgG (from CAPPEL) as a reference standard is added and incubated at room temperature for an hour.

After washing, 100 µl of alkaline phosphatase-labelled human IgG diluted 5,000-fold (from Bio Source) is added and incubated at room temperature for an hour. After washing, a substrate solution is added and incubated. The concentration of the antibody of interest is then calculated by determination of absorbance at 405 nm on the MICROPLATE READER Model 3550 (from Bio-Rad).

The antibody used in the present invention may be an antibody conjugated with any of various molecules including polyethylene glycol (PEG), a radioactive substance, and a toxin. Such a conjugated antibody can be obtained by chemically modifying the antibody produced as described above. The methods of modifying an antibody have been established in the art. The "antibody" in the present invention includes also the conjugated antibodies.

The antibody according to the present invention includes not only a divalent antibody as typified by IgG, but also a monovalent antibody and a polyvalent antibody as typified by IgM as long as the antibody binds Arid5A. The polyvalent antibody according to the present invention includes a polyvalent antibody whose antigen binding sites are all the same or a polyvalent antibody whose antigen binding sites are different in part or in whole.

The antibody according to the present invention may be a bispecific antibody as long as the antibody binds Arid5A. The bispecific antibody refers to an antibody having variable regions that recognize different epitopes, within a single antibody molecule. The epitopes may be present in different molecules or in a single molecule. In other words, the bispecific antibody in the present invention can have antigen binding sites that recognize different epitopes in Arid5A. The bispecific antibody can also have one recognition site recognizing Arid5A and the other recognition site recognizing an antigen except Arid5A.

The methods for producing bispecific antibodies are known. For example, a bispecific antibody can be produced by combining two antibodies that recognize different antigens. Each of the antibodies to be combined may be a half molecule of an antibody having H chain or L chain or a quarter molecule of an antibody consisting of only H chain. Alternatively, a fusion cell producing a bispecific antibody may be produced by fusing hybridomas that each produces different monoclonal antibodies. Furthermore, bispecific antibodies can be produced with genetic engineering techniques.

The antibody according to the present invention may be a low molecular weight antibody as long as the antibody binds Arid5A. The low molecular weight antibody includes an antibody fragment lacking a portion of a whole antibody, such as whole IgG. An antibody molecule may lack some portions as long as the antibody molecule binds Arid5A. The antibody fragments in the present invention preferably comprise either a heavy chain variable region (VH) or a light chain variable region (VL), or both. The amino acid sequence of the VH or VL can have addition, deletion, and/or substitution. The antibody fragments may further lack either VH or VL, or a part of both as long as the antibody fragments binds Arid5A. The antibody fragments may be also chimerized or humanized. Specific examples of the antibody fragment can include, for example, Fab, Fab', F(ab')2, and Fv. Specific examples of the low molecular weight antibody can include, for example, Fab, Fab', F(ab')2, Fv, a single-chain Fv (scFv), Diabody, and a single-chain (Fv)2 (sc(Fv)2). The antibody according to the present invention includes multimers (e.g., dimer, trimer, tetramer, and polymer) of these antibodies.

Antibody fragments can be produced by digesting an antibody with an enzyme. Enzymes known to produce antibody fragments include, for example, papain, pepsin, and plasmin. Alternatively, antibody fragments can be produced by constructing DNAs encoding the antibody fragments, inserting the DNAs into expression vectors, and then allowing the expression vectors to be expressed in suitable host cells (e.g., Co M. S. et al., J. Immunol. (1994) 152, 2968-2976, Better M. & Horwitz A. H., Methods in Enzymology (1989) 178, 476-496, Pluckthun A. & Skerra A., Methods in Enzymology (1989) 178, 497-515, Lamoyi E., Methods in Enzymology (1986) 121, 652-663, Rousseaux J. et al., Methods in Enzymology (1986) 121, 663-669, Bird R. E. & Walker B. W., Trends Biotechnol. (1991) 9, 132-137).

Each of the enzymes for digestion cleaves an antibody at the specific position to provide antibody fragments having specific structures as described below. On the other hand, genetic engineering techniques can be used to delete any portion of an antibody:
in papain digestion: Fab;
in pepsin digestion: F(ab')2 or F(ab'); and
in plasmin digestion: Facb An scFv is obtained by linking a VH and a VL of an antibody. In an scFv, the VH and VL are linked by a linker, preferably a peptide linker (Huston J. S. et al., Proc. Natl. Acad. Sci. USA (1988) 85, 5879-5883). The VH and VL in an scFv may be derived from any antibody described herein. The peptide linker linking V regions is not particularly limited. Any single-stranded peptide, for example, consisting of about 3 to 25 residues, may be used for the linker.

The V regions can be linked by, for example, PCR as described above. For the linking of V regions by PCR, a DNA encoding a full or desired partial amino acid sequence encoded by a DNA sequence encoding an H chain or the V region of an H chain of an antibody and a DNA sequence encoding an L chain or the V region of an L chain of an antibody is used as a template. Each of the DNAs encoding the V region of H chain and L chain is amplified by PCR using primers having sequences corresponding to the sequences at both ends of the DNA to be amplified. A DNA encoding a peptide linker is then prepared. The DNA encoding the peptide linker can be also synthesized by PCR. The primers used in this PCR have base sequences, which can connect to each of the amplified products of the V regions separately synthesized, previously added to the 5' end of the primers. Next, a PCR reaction is performed using each of the DNAs of [VH DNA], [peptide linker DNA], and [VL DNA] with primers for assembly PCR. The primers for the assembly PCR are a combination of a primer that can anneal to the 5' end of [VH DNA] and a primer that can anneal to the 3' end of [VL DNA]. In other words, the primers for the assembly PCR comprise a set of primers that can be used to amplify a DNA encoding the full sequence of the scFv to be synthesized. The [peptide linker DNA] has a base sequence previously added, which can connect to each of the DNAs of the V regions. The primers for the assembly PCR are used to link these DNAs, eventually producing the full-length scFv as an amplified product. Once the DNA encoding the scFv is produced, an expression vector comprising the DNA and recombinant cells transformed with the expression vector can be obtained using any conventional method. The scFv can be also obtained by culturing the resulting recombinant cells and allowing the cells to express the DNA encoding the scFv.

Diabody refers to a bivalent low molecular weight antibody constructed by gene fusion (Holliger P. et al., Proc. Natl. Acad. Sci. USA (1993) 90, 6444-6448, EP 404097, WO 93/11161). Diabody is a dimer composed of two polypeptide chains. Generally, each of the polypeptide chains composing the dimer is linked by a linker between VL and VH in a single chain. The linker for the polypeptide chains in the diabody typically is too short to allow the VL and VH on the same chain to associate with each other. Specifically, amino acid residues composing the linker has preferably 2 to 12 residues, more preferably 3 to 10 residues, and particularly about 5 residues. Therefore, the VL and VH encoded in a single polypeptide chain are not able to form an scFv and therefore two separate polypeptide chains result in dimerization to form two Fvs. Consequently, the diabody has two antigen binding sites.

An sc(Fv)2 is a single-stranded low molecular weight antibody, in which two VHs and two VLs are linked by linkers (Hudson P. J. & Kortt A. A., J. Immunol. Methods (1999) 231, 177-189). An sc(Fv)2 can be produced, for example, by linking two scFvs by a linker. Alternatively, an sc(Fv)2 can be also produced by linking two VHs and two VLs by linkers, starting from the N-terminus of the single-stranded polypeptide, in the order as described below:
[VH]-[linker]-[VL]-[linker]-[VH]-[linker]-[VL].
It is noted that the order of two VHs and two VLs is not particularly limited to the order as described above and any order is acceptable. For example, the orders as described below can be also included.
[VL]-[linker]-[VH]-[linker]-[VH]-[linker]-[VL]
[VH]-[linker]-[VL]-[linker]-[VL]-[linker]-[VH]
[VH]-[linker]-[VH]-[linker]-[VL]-[linker]-[VL]
[VL]-[linker]-[VL]-[linker]-[VH]-[linker]-[VH]
[VL]-[linker]-[VH]-[linker]-[VL]-[linker]-[VH]
A plurality of the linkers may be the same or different type.

The linkers that can be used to link variable regions of an antibody include any peptide linker that can be incorporated by genetic engineering or a synthetic compound linker (e.g., the linker disclosed in Protein Engineering (1996) 9, 299-305). Peptide linkers are preferred in the present invention. The length of peptide linkers is not particularly limited and can be appropriately selected by those skilled in the art according to any purpose. Generally, amino acid residues composing a peptide linker have 1 to 100 amino acids, preferably 3 to 50 amino acids, more preferably 5 to 30 amino acids, particularly preferably 12 to 18 amino acids (e.g., 15 amino acids). An amino acid sequence composing a peptide linker can be any sequence unless the sequence inhibits the binding effect of scFv.

Alternatively, synthetic compound linkers (chemical cross-linkers) can be also used to link V regions. Cross-linkers that are commonly used for cross-linking of peptide compounds can be used in the present invention. The cross-linkers that can be used include, for example, N-hydroxysuccinimide (NHS), disuccinimidyl suberate (DSS), bis(sulfosuccinimidyl)suberate (BS3), dithiobis(succinimidyl propionate) (DSP), dithiobis(sulfosuccinimidyl propionate) (DTSSP), ethylene glycol bis(succinimidyl succinate) (EGS), ethylene glycol bis(sulfosuccinimidyl succinate)(sulfo-EGS), disuccinimidyl tartrate (DST), disulfosuccinimidyl tartrate (sulfo-DST), bis[2-(succinimide oxycarbonyloxy)ethyl]sulfone (BSOCOES), and bis[2-(sulfosuccinimideoxycarbonyloxy)ethyl] sulfone (sulfo-BSOCOES).

The therapeutic or prophylactic agent for a lung disease in the present invention may include a pharmaceutically acceptable material such as a preservative or a stabilizer. The term pharmaceutically acceptable means a pharmaceutically acceptable material that by itself may or may not be therapeutically effective for a lung disease and can be administered in combination with the therapeutic agent as described above. The pharmaceutically acceptable material may also be a material that is not therapeutically effective but has a synergistic or additive stabilizing effect in combination with an Arid5A inhibitor.

The pharmaceutically acceptable materials include, for example, sterile water, physiological saline, a stabilizer, an excipient, a buffering agent, an antiseptic, a surfactant, a chelating agent (e.g., EDTA), and a bonding agent.

The surfactants in the present invention can include nonionic surfactants typically including, for example, sorbitan fatty acid esters such as sorbitan monocaprylate, sorbitan monolaurate, and sorbitan monopalmitate; and glycerol fatty acid esters having HLB 6 to 18 such as glyceryl monocaprylate, glyceryl monomyristate, and glyceryl monostearate.

The surfactants can also include anionic surfactants typically including, for example, alkyl sulfates, in which the alkyl group has 10 to 18 carbon atoms, such as sodium cetyl sulfate, sodium lauryl sulfate, and sodium oleyl sulfate; polyoxyethylene alkyl ether sulfates, in which the average number of moles added of the ethylene oxide is from 2 to 4 and the alkyl group has 10 to 18 carbon atoms, such as polyoxyethylene sodium lauryl sulfate; alkyl sulfosuccinate ester salts, in which the alkyl group has 8 to 18 carbon atoms, such as sodium lauryl sulfosuccinate ester; natural surfactants, such as lecithin and glycerophospholipid; sphingophospholipids such as sphingomyelin; and sucrose fatty acid esters in which the fatty acid has 12 to 18 carbon atoms.

The agents according to the present invention can include one or more than one surfactant as described above in combination. The preferred surfactants used in the formulation according to the present invention are polyoxyethylene sorbitan fatty acid esters, such as polysorbate 20, 40, 60, or 80, and polysorbate 20 and 80 are particularly preferred. Polyoxyethylene-polyoxypropylene glycols as typified by poloxamer (e.g., Pluronic F-68 (R)) are also preferred.

The buffering agent in the present invention can include phosphoric acid, citrate buffer, acetic acid, malic acid, tartaric acid, succinic acid, lactic acid, potassium phosphate, gluconic acid, caprylic acid, deoxycholic acid, salicylic acid, triethanolamine, fumaric acid, and other organic acids, or carbonate buffer, tris buffer, histidine buffer, and imidazole buffer.

Liquid formulations may be also prepared by dissolving the agents according to the present invention in aqueous buffers known in the art of liquid formulation. The buffers have generally a concentration of 1 to 500 mM, preferably 5 to 100 mM, and more preferably 10 to 20 mM.

The agents according to the present invention may include other low molecular weight polypeptides, proteins such as serum albumin, gelatin, and immunoglobulin, amino acids, saccharides such as polysaccharides and monosaccharides, carbohydrates, and sugar alcohols.

In the present invention, saccharides, such as polysaccharide and monosaccharide, and carbohydrates include, for example, dextran, glucose, fructose, lactose, xylose, mannose, maltose, sucrose, trehalose, and raffinose.

In the present invention, sugar alcohols can include, for example, mannitol, sorbitol, and inositol.

When used as an aqueous solution for injection, the agents according to the present invention may be combined with, for example, physiological saline, an isotonic solution containing glucose or other adjuvants e.g., D-sorbitol, D-mannose, D-mannitol, and sodium chloride, a suitable dissolution aid, for example, alcohols (e.g., ethanol), polyalcohols (e.g., propylene glycol, PEG), and nonionic surfactants (e.g., polysorbate 80, HCO-50).

The agents according to the present invention may further comprise a diluent, a dissolution aid, a pH adjusting agent, a soothing agent, a sulfur-containing reducing agent, an antioxidant, and the like, as desired.

If necessary, the agents according to the present invention may be also encapsulated in microcapsules (microcapsules made of hydroxymethyl cellulose, gelatin, poly[methyl methacrylic acid], or the like) or may be adapted for colloidal drug delivery systems (such as liposome, albumin microsphere, microemulsion, nanoparticle, and nanocapsule) (see e.g., "Remington's Pharmaceutical Science 16th edition", Oslo Ed., 1980). Moreover, methods for converting an agent to a sustained-release agent are known and are applicable to the present invention (Langer et al., J. Biomed. Mater. Res. 1981, 15: 167-277; Langer, Chem. Tech. 1982, 12: 98-105; U.S. Pat. No. 3,773,919; European patent application publication No. (EP) 58,481; Sidman et al., Biopolymers 1983, 22: 547-556; EP133,988).

Pharmaceutically acceptable carriers to be used are appropriately selected from, but not limited to, those as described above or a combination thereof depending on the dosage form.

The Arid5A inhibitor according to the present invention can be used as a pharmaceutical for human or other animals not only by directly administering the substance to patients but also by administering a formulation formulated using any known pharmaceutical method. For formulation, a pharmaceutically acceptable material as described above may be added.

All agents in the present invention can be administered orally, parenterally, systemically, or locally in the form of pharmaceutical preparation. The route of administration can be appropriately selected from, for example, intravenous injection including infusion, intramuscular injection, intraperitoneal injection, subcutaneous injection, a suppository, intestinal infusion, and an oral enteric-coated formulation, depending on age and condition of a patient. An effective dosage is selected from the range from 0.001 mg to 100 mg per kg of body weight per dose. Alternatively, a dosage can be selected from the range from 0.1 to 1,000 mg, preferably 0.1 to 50 mg per patient. For example, the effective dosage for anti-Arid5A antibody is an amount that results in free antibody present in blood, and specific examples of the preferred dosage and route of administration include 0.1 mg to 40 mg, preferably 1 mg to 20 mg per kg of body weight per month (4 weeks) as a single dose or divided doses, for example, a schedule for administration including twice a week, once a week, once every two weeks, and once every four weeks, by intravenous injection including infusion, subcutaneous injection, or the like. The schedule for administration can be adjusted, for example, by extending the interval between doses from twice a week or once a week to once every two weeks, once every three weeks, or once every four weeks while the condition of patient and the values of blood tests following doses are observed.

The lung disease according to the present invention include a wide range of diseases affecting lung and respiratory tract, for example, acute bronchitis, bacterial pneumonia, lung abscess, pulmonary tuberculosis, atypical mycobacterial lung infection, fungal lung disease, parasitic lung disease, opportunistic infection (Pneumocystis pneumonia, cytomegalovirus pneumonitis), aspiration pneumonia, common cold syndrome, infectious respiratory diseases such as influenza; airway obstructive diseases such as chronic obstructive pulmonary disease (COPD) and diffuse panbronchiolitis; allergic lung diseases such as bronchial asthma, hypersensitivity pneumonitis, eosinophilic pneumonitis, allergic bronchopulmonary aspergillosis, drug-induced pneumonia, and eosinophilic granulomatosis with polyangiitis; interstitial lung diseases such as idiopathic interstitial pneumonia, radiation pneumonitis, sarcoidosis, idiopathic organizing pneumonia, and lung disease related to collagen vascular disease; neoplastic lung diseases such as lung cancer, metastatic lung tumor, pulmonary benign tumor, and mediastinal neoplasm; pulmonary vascular lesions such as pulmonary thromboembolism, pulmonary arterial pulmonary hypertension, and pulmonary edema;

pleural diseases such as pleurisy, pyothorax, pleural tumors, and pneumothorax; and respiratory failure such as acute respiratory distress syndrome (ARDS) and chronic respiratory distress syndrome.

The therapeutic and/or prophylactic agent for a lung disease according to the present invention also provide(s) agents useful for the treatment of pulmonary fibrosis that is not limited by causes of the lung diseases as described above. Pulmonary fibrosis is a disease characterized by diffuse fibroplasia of the alveolar walls and main symptoms of dry cough and exertional dyspnea. Pulmonary fibrosis refers to an end-stage disease state of interstitial pneumonia in a narrow sense while it means a co-existing state of pulmonary fibrosis and interstitial pneumonia in a broad sense.

The present invention relates to a method for screening for a pharmaceutical composition for treating or preventing a lung disease by suppressing the expression and/or function of Arid5A.

The method for screening according to the present invention first comprises detecting an effect of test agents on the expression and/or function of Arid5A. The function of Arid5A includes, for example, contribution to stabilization of IL-6 mRNA by specifically binding to the stem-loop of IL-6 mRNA and antagonistically inhibiting the action of Regnase-1, which specifically destroys IL-6 mRNA. Accordingly, the effect on the expression and/or function of Arid5A include, but are not limited to, for example, suppression of the expression of Arid5A, inhibition of the function of Arid5A by binding to Arid5A, and inhibition of the function of Arid5A by binding competitively with Arid5A to IL-6 mRNA.

The screening method also comprises selecting the agents that decrease the expression and/or function as compared to the absence of the test agents.

In the first aspect of the screening method according to the present invention, Arid5A is first contacted with test agents.

The amino acid sequence of human Arid5A used in the method according to the present invention is as described above. The Arid5A used in the method according to the present invention includes a protein functionally equivalent to the known Arid5A as described above. Such a protein includes, but is not limited to, for example, a mutant, allele, variant, and homolog of Arid5A, a partial peptide of Arid5A, or a fusion protein with another protein.

The mutant of Arid5A in the present invention can include a protein that is a naturally occurring protein consisting of an amino acid sequence in which one or more amino acids in the amino acid sequence as described above are substituted, deleted, inserted, and/or added and is functionally equivalent to the protein consisting of the amino acid sequence as described above. The mutant of Arid5A can also include a protein that is encoded by a naturally occurring DNA hybridizing to a DNA consisting of the base sequence as described above under a stringent condition and is functionally equivalent to a protein consisting of the amino acid sequence as described above.

In the present invention, the number of mutated amino acids is not particularly limited but should be typically 30 amino acids or less, preferably 15 amino acid or less, more preferably 5 amino acids or less (for example, 3 amino acids or less). When mutated, the amino acid residues are desirably mutated to other amino acids having preserved side chain properties. For example, the properties of amino acid side chains can include hydrophobic amino acids (A, I, L, M, F, P, W, Y, V), hydrophilic amino acids (R, D, N, C, E, Q, G, H, K, S, T), amino acids having aliphatic side chains (G, A, V, L, I, P), amino acids having side chains containing hydroxy groups (S, T, Y), amino acids having side chains containing sulfur atoms (C, M), amino acids having side chains containing carboxylic acids and amides (D, N, E, Q), amino acids having side chains containing bases (R, K, H), and amino acids having aromatic side chains (H, F, Y, W) (each letter in parentheses represents one-letter notation for amino acids). Even though a polypeptide has an amino acid sequence modified with deletion and/or addition of one or more amino acid residues, and/or substitution with other amino acid sequences for an amino acid sequence, the polypeptide is known to maintain its biological activity.

"Functionally equivalent" in the present invention refers to a protein of interest having a biological or biochemical function equivalent to Arid5A. Arid5A contributes to stabilization of IL-6 mRNA by specifically binding to the stem-loop of IL-6 mRNA and antagonistically inhibiting the action of Regnase-1, which specifically destroys IL-6 mRNA. The biological or biochemical function of Arid5A in the present invention can include stabilization of IL-6 mRNA.

Methods well known to those skilled in the art for preparing a DNA encoding "a protein functionally equivalent to" a protein of interest, include methods using a hybridization technique and a polymerase chain reaction (PCR) technique. In other words, those skilled in the art generally could isolate a DNA that has high homology to Arid5A by using the base sequence of Arid5A or a part thereof as a probe and an oligonucleotide specifically hybridizing to Arid5A as a primer. The DNA in the present invention also includes a DNA encoding a protein having a function equivalent to Arid5A that can be isolated by using such hybridization technique and PCR technique.

The isolation of DNA is achieved by a hybridization reaction preferably under a stringent condition. The stringent hybridization condition in the present invention refers to a condition in 6M urea, 0.4% SDS, 0.5×SSC or a hybridization condition of stringency equivalent thereto. A condition of higher stringency, for example, a condition in 6M urea, 0.4% SDS, 0.1×SSC can be used to isolate a DNA having higher homology to Arid5A. The DNA isolated under this condition should have high homology to an amino acid sequence of the protein of interest in the amino acid level. The high homology refers to a sequence identity of at least 50% or more, more preferably 70% or more, and even preferably 90% or more (e.g., 95%, 96%, 97%, 98%, 99%, or more) throughout the amino acid sequence. The identity of amino acid sequences and base sequences can be determined using the algorithm BLAST by Karlin and Altschul (Proc. Natl. Acad. Sci., ISA 87: 2264-2268, 1990, Proc Natl Acad Sci USA 90: 5873, 1993). Programs, called BLASTN and BLASTX, based on the algorithm of BLAST have been developed (Altschul S F, et al: J Mol Biol 215: 403, 1990). BLASTN is performed to analyze base sequences using parameters, for example, score=100, word length=12. BLASTX is performed to analyze amino acid sequences using parameters, for example, score=50, word length=3. BLAST and Gapped BLAST programs are performed using the default parameters of each program. Specific procedures of these analyses are known.

The species of organisms from which Arid5A used in the method according to the present invention is derived is not limited to a particular species of organism. The species of organisms includes, for example, human, monkey, mouse, rat, guinea pig, pig, cattle, yeast, and insect.

The form of Arid5A used in the first aspect is not particularly limited. Arid5A may be, for example, in a purified form, in a form expressed within cells, and in a form expressed in cell extracts.

Arid5A can be purified using any well-known method. Cells expressing Arid5A include cells expressing endogenous Arid5A or cells expressing foreign Arid5A. The cells expressing endogenous Arid5A include, but are not limited to, cells from tissues of animals and cultured cells. The cultured cells are not particularly limited and may be, for example, commercially-available cells. The species of organisms from which the cells expressing endogenous Arid5A is derived is not particularly limited, but includes human, monkey, mouse, rat, guinea pig, pig, cattle, yeast, and insect. The cells expressing foreign Arid5A can be produced, for example, by transducing a vector comprising a DNA encoding Arid5A into cells. The transduction of the vector into cells can be performed using any conventional method, such as, calcium phosphate precipitation, electroporation, Lipofectamine method, and microinjection. The cells comprising foreign Arid5A can be also produced, for example, by inserting a DNA encoding Arid5A into a chromosome using a gene transfer technique utilizing homologous recombination. The species of organisms from which the cells transduced with foreign Arid5A are derived is not particularly limited to mammals and may be any species of organisms that has an established technique to cause intracellular expression of a foreign protein.

Cell extracts containing the expressed Arid5A include, for example, a cell extract containing an in vitro transcription-translation system and a vector comprising a DNA encoding Arid5A. The in vitro transcription-translation system is not particularly limited and may be any commercially-available in vitro transcription-translation kit.

"Test agents" in the present invention are not particularly limited and can include, for example, a single substance such as a natural compound, an organic compound, an inorganic compound, a nucleic acid, a protein, and a peptide, and an expression product from a compound library, a nucleic acid library, a peptide library, or a gene library, a cell extract, a cell culture supernatant, a product from fermentation microorganisms, an extract of marine organisms, a plant extract, a prokaryotic cell extract, an extract of eukaryotic unicellular organisms, and an animal cell extract. The test agents can be appropriately labeled and used as necessary. The labels include, for example, a radioactive label and a fluorescent label. "Test agents" in the present invention may include only one of the test agents as listed above or may include a mixture of a plurality of the test agents.

"Contacting" in the present invention is performed depending on the form of Arid5A. For example, when Arid5A is in a purified form, the contacting can be performed by adding a test agent to a purified preparation. When Arid5A is in a form expressed within cells or in a form expressed in cell extracts, the contacting can be performed by adding a test agent to the cell culture medium or the cell extract respectively, or by directly administering test agents to experimental animals. When the test agent is a protein, the contacting can be also performed, for example, by transducing a vector comprising a DNA encoding the protein into cells expressing Arid5A or by adding the vector to an extract of cells expressing Arid5A. For example, the two-hybrid method using yeast or animal cells may also be used.

In the first aspect, the expression and/or function of Arid5A is then determined. The function of Arid5A can include stabilization of IL-6 mRNA. Specifically, the function of Arid5A can be indirectly determined, for example, by contacting Arid5A with test agents and determining a suppressing effect on the degradation of IL-6 mRNA. Test agents that decrease or increase the expression and/or function as compared to the absence of the test agents are then selected. When test agents are administered to experimental animals, a tissue such as spleen is removed and the expression and/or function of Arid5A or the expression level of IL-6 mRNA is determined in particular cells such as macrophage. The expression level can be determined using a technique appropriately selected from an amplification-based technique such as polymerase chain reaction (PCR), reverse transcription-polymerase chain reaction (RT-PCR), or real time PCR, a hybridization-based technique, and/or other detection techniques. "PCR" in the present application includes techniques determining various DNAs and RNAs by PCR and amplification-based techniques derived therefrom. It is known that inhibition of Arid5A expression within cells will suppress the expression of IL-6 mRNA and will have no effect on the expression of TNF-α mRNA because Arid5A is a protein that contributes to stabilization of IL-6 mRNA. The screening of test agents can be achieved by confirming that the test agents have effects on the expression of IL-6 mRNA and no effect on the expression of TNF-α mRNA. Consequently, the test agents having an effect on Arid5A expression are selected, and thus the test agents having the effect of treating or preventing a lung disease are selected. The selected test agents include an agent that decreases the expression and/or function of Arid5A and thus should have an effect of treating or preventing a lung disease by suppressing the expression and/or function of Arid5A.

In the second aspect, Arid5A is first contacted with a test agent and then the binding of Arid5A to the test agent is detected. The detection method is not particularly limited. The binding of Arid5A to the test agents can be detected, for example, by detecting a label (e.g., a label that can be quantitatively determined, such as a radioactive label and a fluorescent label) attached to the test agents bound to Arid5A. A labeling agent may be also attached to Arid5A. The binding can be also detected by immobilizing test agents or Arid5A onto a resin, chip, or the like. The binding can be also detected based on the change of Arid5A function due to the binding of Arid5A to test agents.

In this aspect, test agents that bind to Arid5A are then selected. The selected test agents include an agent that decreases the expression or function of Arid5A and thus the selected test agents should have the effect of treating or preventing a lung disease by suppressing the expression or function of Arid5A.

In the third aspect of the method for screening according to the present invention, cells expressing Arid5A are first contacted with a test agent and then the expression level of Arid5A is measured. The expression level of Arid5A can be measured using any method known to those skilled in the art. The transcriptional level of the gene can be measured, for example, by extracting mRNA of the gene according to any conventional method and performing Northern hybridization or RT-PCR using the mRNA as a template. The expression level of the gene can be further measured using a DNA array technique.

The translation level of gene can be also measured by collecting a fraction containing Arid5A encoded by the gene according to any conventional method and detecting the expression of Arid5A using electrophoresis such as SDS-PAGE. The translation level of gene can be also measured by performing Western blotting with an antibody directed against Arid5A to detect the expression of Arid5A. The antibody directed against Arid5A may be an antibody as described above.

In the third aspect, the test agents that decrease the expression level of Arid5A as compared to the absence of the test agents are then selected. The selected agents include an agent that decreases the expression of Arid5A, and thus the selected agents should have the effect of treating or preventing a lung disease by suppressing the expression of Arid5A. It is known that inhibition of Arid5A expression within cells will suppress the expression of IL-6 mRNA and will have no effect on the expression of TNF-α mRNA because Arid5A is a protein that contributes to stabilization of IL-6 mRNA. The screening of test agents can be achieved by confirming that the test agents have an effect on the expression of IL-6 mRNA and no effect on the expression of TNF-α mRNA. Consequently, the test agents having an effect on Arid5A expression are selected, and thus the test agents having the effect of treating or preventing a lung disease are selected.

In the fourth aspect of the screening method according to the present invention, provided are cells or cell extracts that have a DNA operably linked to a reporter gene downstream of the promoter region of the DNA encoding Arid5A.

In the fourth aspect, "operably linked" refers to the linking between the promoter region of Arid5A gene and a reporter gene to result in the expression of the reporter gene induced by binding of a transcription factor to the promoter region of Arid5A gene. Thus, the meaning of the term "operably linked" includes an expression of a fusion protein induced by binding a transcription factor to the promoter region of Arid5A gene even though a reporter gene is linked to another gene to form a fusion protein with another gene product.

The reporter gene is not particularly limited as long as its expression is detectable. The reporter gene includes, for example, CAT gene, lacZ gene, luciferase gene, β-glucuronidase gene (GUS), and GFP gene, which are commonly used by those skilled in the art. The reporter gene also includes a DNA encoding Arid5A.

Cells or cell extracts that have a DNA operably linked to a reporter gene downstream of the promoter region of the DNA encoding Arid5A can be prepared using the above-mentioned methods.

In the fourth aspect, the cells or cell extracts are then contacted with test agents. The expression level of the reporter gene in the cells or cell extracts is measured.

The expression level of the reporter gene can be measured using any method known to those skilled in the art depending on the type of the reporter gene used. For example, when the reporter gene is CAT gene, the expression level of the reporter gene can be measured by detecting chloramphenicol acetylated by the product of the gene. When the reporter gene is lacZ gene, the expression level of the reporter gene can be measured by detecting the color reaction of the dye compound due to catalysis of the expression product of the gene. When the reporter gene is luciferase gene, the expression level of the reporter gene can be measured by detecting fluorescence from the fluorescent compound due to catalysis of the gene product. When the reporter gene is β-glucuronidase gene (GUS), the expression level of the reporter gene can be measured by detecting luminescence of Glucuron (ICN) or the color reaction of 5-bromo-4-chloro-3-indolyl-β-glucuronide (X-Gluc) due to catalysis the expression product of the gene.

When Arid5A gene is used as a reporter, the expression level of the gene can be measured using any of the methods as described above.

In the fourth aspect, test agents are then selected that decrease or increase the expression level of the reporter gene as compared to the absence of the test agents. The selected test agents include an agent that decreases the expression of Arid5A, and thus the selected test agents should have the effect of treating or preventing a lung disease by suppressing the expression of Arid5A.

In the fifth aspect, IL-6 mRNA is first contacted with a test agent and then the binding of IL-6 mRNA to the test agent is detected. The detection method is not particularly limited. The binding of IL-6 mRNA to the test agents can be detected, for example, by detecting a label (e.g., a label that can be quantitatively determined, such as a radioactive label and a fluorescent label) attached to the test agents bound to IL-6 mRNA. A labeling agent may be also attached to IL-6 mRNA. The binding can be also detected by immobilizing test agents or IL-6 mRNA onto a resin, chip, or the like. The binding can be also detected based on the change of IL-6 mRNA activity due to the binding of IL-6 mRNA to test agents.

In this aspect, test agents that bind to IL-6 mRNA are then selected. The selected test agents include an agent that decreases the expression and/or function of Arid5A, and thus the selected test agents should have the effect of treating or preventing a lung disease by suppressing the expression or function of Arid5A.

In the sixth aspect, IL-6 mRNA is first contacted with a test agent and further contacted with Arid5A, and then the function of Arid5A is determined. The function of Arid5A can be determined in the manner as described above. Test agents that decrease or increase the function as compared to the absence of the test agents are then selected. The selected test agents include an agent that decreases the function of Arid5A and thus should have an effect of treating or preventing a lung disease by suppressing the function of Arid5A.

EXAMPLES

Example 1

Figure 1B:
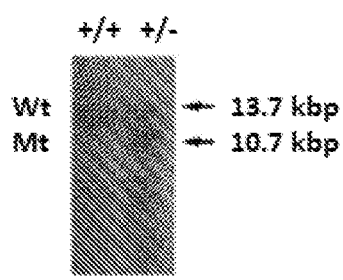

Generation of Arid5A Knockout Mice (FIGS. 1A and 1B)

C57BL/6 wild type mice (aged 6 to 8 weeks) were obtained from CLEA Japan, Inc. Arid5A knockout mice (No. CDB0602K: www.cdb.riken.jp/arg/mutant%20mice%20list.html) were generated using the method described at www.cdb.riken.jp/arg/Methods.html. The targeting vector was constructed by substituting the main part of DNA binding domain of Arid5A gene with Neo-cassette interrupted by lox P sequences at both ends of the Neo-cassette and was transduced into ES cell strain TT2 by electroporation. Gene disruption by homologous recombination was confirmed by Southern blotting with a probe corresponding to the 3' UTR of Arid5A gene. The resulting mutant ES cells were used to generate chimeric mice. Germline transmission of the mutant allele was confirmed by Southern blotting analysis and genomic PCR (primer 1: 5'-ATACTTTCTCGGCAGGAGCA-3'; primer 2: 5'-TGAATGAACTGCAGGACG AG-3') using genomic DNA from offspring mice obtained by crossing the chimeric mice with C57BL mice. The heterozygous mutant mice were raised in a specific pathogen-free environment and were back-crossed with C57BL mice for five generations.

Example 2

Induction of Lung Disorders in Arid5A Knockout Mice (Lung Disease Model)

Arid5A knockout mice (Arid5A −/−) and wild type mice aged 8 to 9 weeks (each mouse has a body weight of 20 to 25 g) intraperitoneally received tribromoethanol (Avertin) for anesthesia at 40 ng per mouse. Subsequently, bleomycin (BLM) was intratracheally instilled at a dose of 2 mg/kg.

Survival Rate

The survival rate of the mice described above was examined for 4 weeks.

Figure 2:
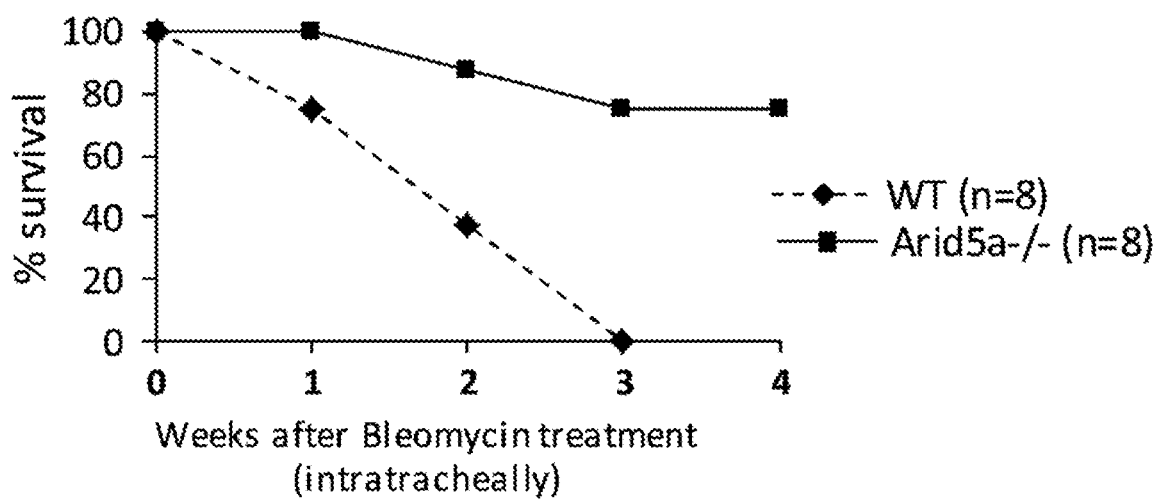
FIG. 2 is a graph showing % survival of Arid5A-deficient mice and wild type mice after inducing lung disorders by intratracheal instillation of bleomycin.

As a result, the survival rate of the wild type mice gradually decreased, and all the wild type mice died after 3 weeks. In contrast, few Arid5A knockout mice developed lung disorders, and their survival rate after 4 weeks was 80% (FIG. 2).

Observation of Lung Tissues

Figure 3A:
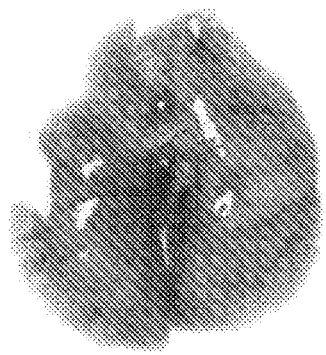
FIGS. 3A and 3B present photographs of lung from an Arid5A-deficient mouse (FIG. 3A) and a wild type mouse (FIG. 3B) at day 7 after intratracheal instillation of bleomycin.
Figure 3B:
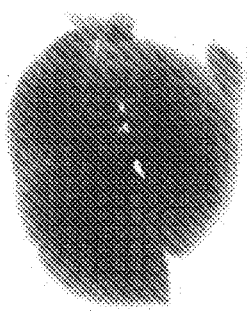

Three and seven days after intratracheal instillation of BLM, 10% neutral phosphate buffered formalin solution was intratracheally administered to the mice as described above and lung tissues were isolated after fixation. Photographs of lung tissues from an Arid5A knockout mouse and a wild type mouse 7 days after administration of BLM are shown in FIGS. 3A and 3B. Moreover, isolated lung tissues were embedded in paraffin and sliced into 6 μm thick sections which were stained with hematoxylin and eosin (H&E) (FIGS. 4A and 4B).

Figure 4A:
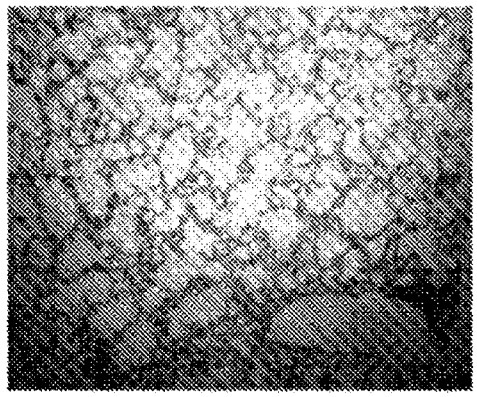
FIGS. 4A and 4B present hematoxylin-eosin stained images of lung tissue sections from an Arid5A-deficient mouse (FIG. 4A) and a wild type mouse (FIG. 4B) at day 7 after intratracheal instillation of bleomycin.
Figure 4B:
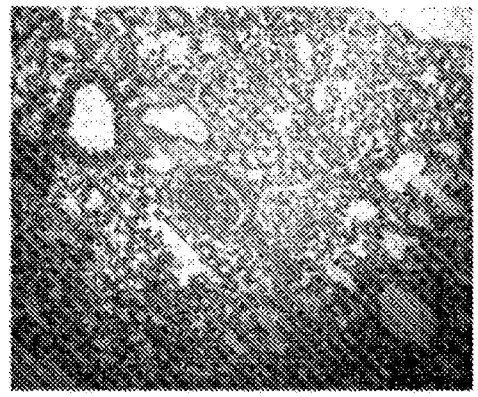

As a result, the lung from the wild type mouse had inflammation and atrophy due to intratracheal instillation of BLM and accumulation of neutrophils was observed (FIG. 3B, FIG. 4B) whereas the condition of the lung from the Arid5A knockout mouse remained the same as that of normal lung (FIG. 3A, FIG. 4A).

Preparation and Analysis of Lung Lavage Fluids

Lung lavage fluids 7 days after intratracheal instillation of BLM (BAL fluids) were collected in order to evaluate the accumulation of inflammatory cells in pulmonary alveoli. Specifically, mice were tracheally intubated and instilled with 1.5 mL of sterile physiological saline, and lavage fluids were then collected in two portions. This procedure was performed a total of 3 times per mouse. The amount of lung lavage fluids collected was on average about 90% of the instilled amount. The collection rates of lavage fluids were substantially constant regardless of treatment conditions or types of mice (wildtype and Arid5A knockout mice). The collected lung lavage fluids were centrifuged at 300×g for 10 minutes to collect cells which were counted with a hemocytometer. The fraction of white blood cells was evaluated based on a cytological preparation. Specifically, slides were prepared using Cytospin (TOMY SEIKO CO., LTD., Tokyo, Japan) and stained with Diff-Quik (from SYSMEX INTERNATIONAL REAGENTS CO., LTD.). The amounts of IL-6, TNFα, and IFNγ in lung lavage fluids were also measured (FIG. 5).

Figure 5:
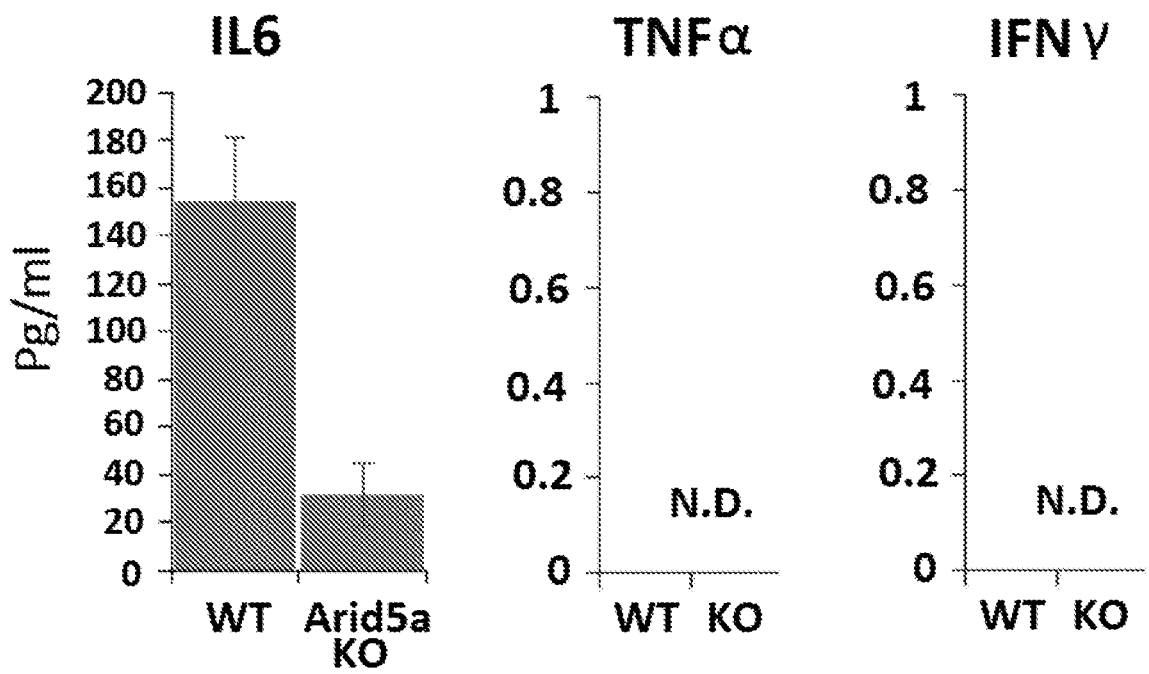
FIG. 5 shows the amounts of IL6, TNF, and IFN-γ in lung lavage fluids from Arid5A-deficient mice and wild type mice at day 7 after intratracheal instillation of bleomycin.

As a result, as shown in FIG. 5, wild type mice had IL-6 concentration of about 150 pg/mL, which were detected in lung lavage fluids 7 days after intratracheal instillation of BLM, while Arid5A knockout mice had IL-6 concentration of about 30 pg/mL. No TNFα and IFNγ were detected in both wild type mice and Arid5A knockout mice.

Example 3

Control of IL-6 Expression Controlled by Arid5A siRNA

Figure 6:
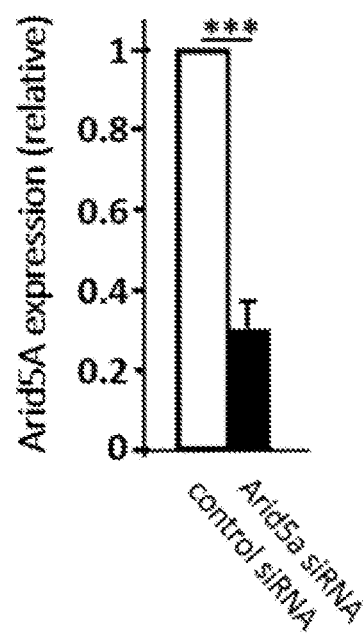
FIG. 6 is a graph showing the levels of Arid5A mRNA quantified by qPCR in a macrophage cell line.
Figure 7:
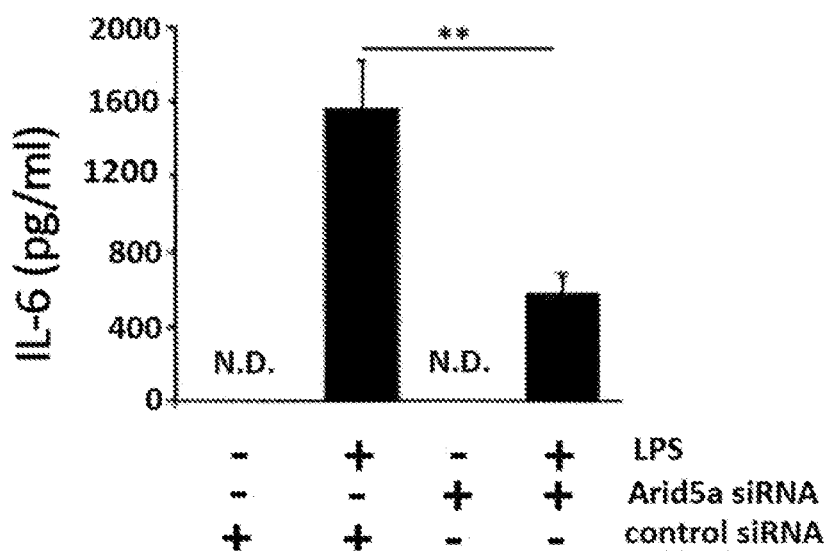
FIG. 7 is a graph showing the concentrations of IL-6 measured by ELISA in culture supernatants of a macrophage cell line.
Figure 8:
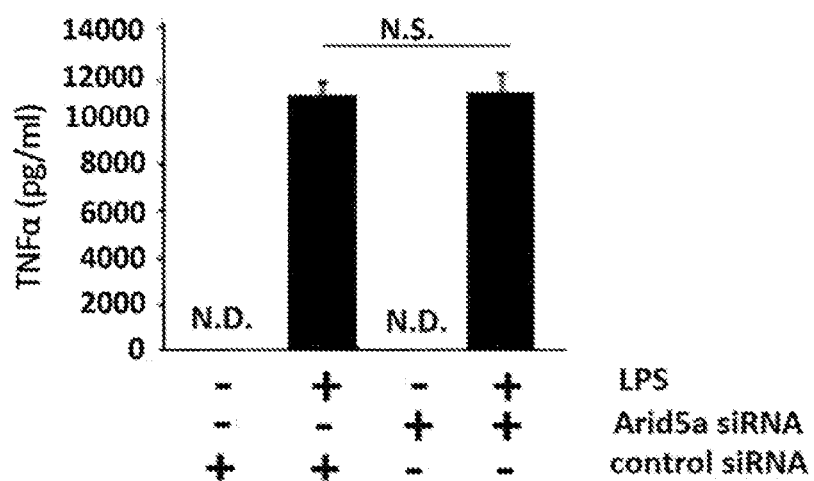
FIG. 8 is a graph showing the concentrations of TNF-α measured by ELISA in culture supernatants of a macrophage cell line.

The murine macrophage cell line RAW 264.7 was transduced with Arid5A siRNA (SASI_Mm02_00341523 (sigma)) or a control siRNA (100 nM) by electroporation. After culturing for 24 hours, the cells were stimulated with LPS (100 ng/mL) for 24 hours. RNA was extracted from the resulting cells. The level of Arid5A mRNA was quantified by qPCR (FIG. 6). The concentrations of IL-6 and TNF-α in each culture supernatant were quantified by ELISA (FIGS. 7 and 8). As shown in FIG. 6, the transduction of Arid5A siRNA into RAW 264.7 markedly decreased the expression level of Arid5A mRNA. As shown in FIG. 7 and FIG. 8, in the cells transduced with Arid5A siRNA, the amount of IL-6 produced in response to LPS stimulation was decreased whereas the amount of TNF-α remained unchanged.

Example 4

Figure 9:
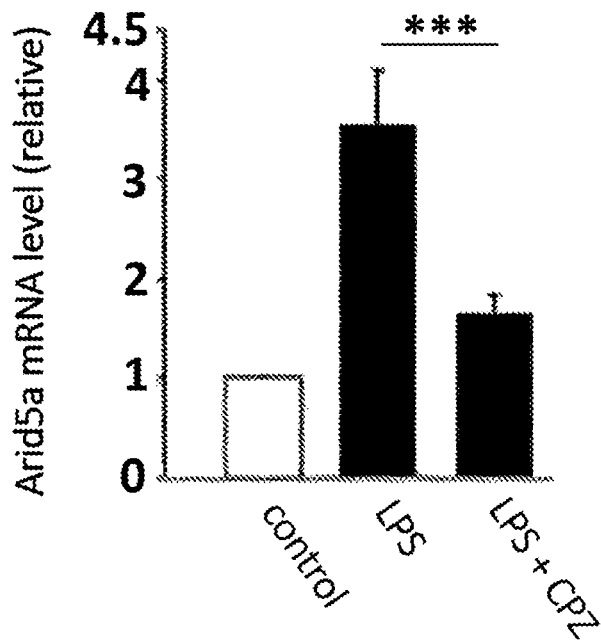
FIG. 9 is a graph showing mRNA expression of Arid5A in peritoneal macrophages.
Figure 10:
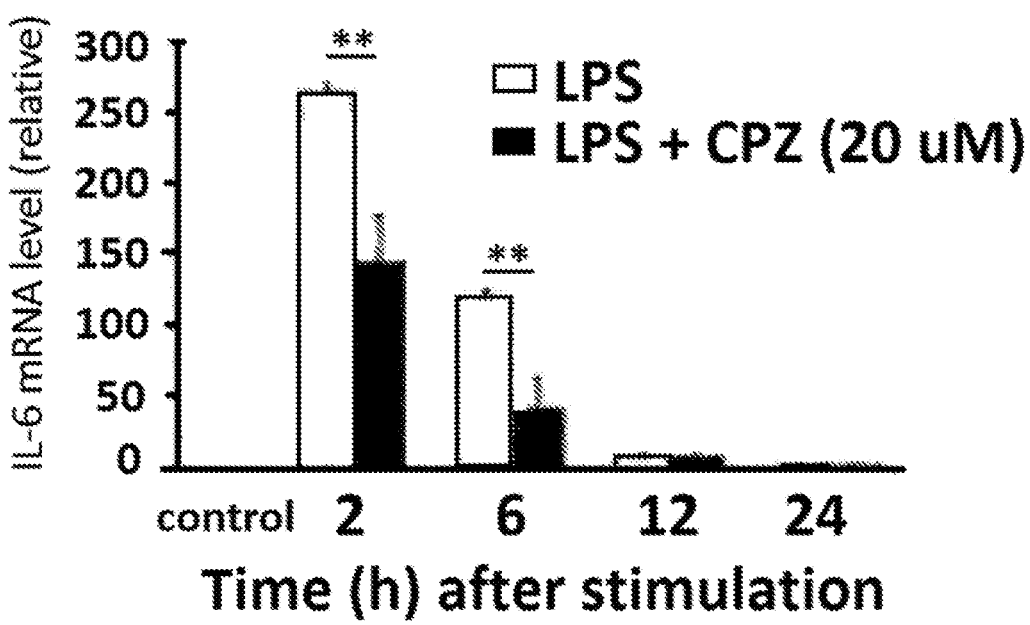
FIG. 10 is a graph showing mRNA expression of IL-6 in peritoneal macrophages.
Figure 11:
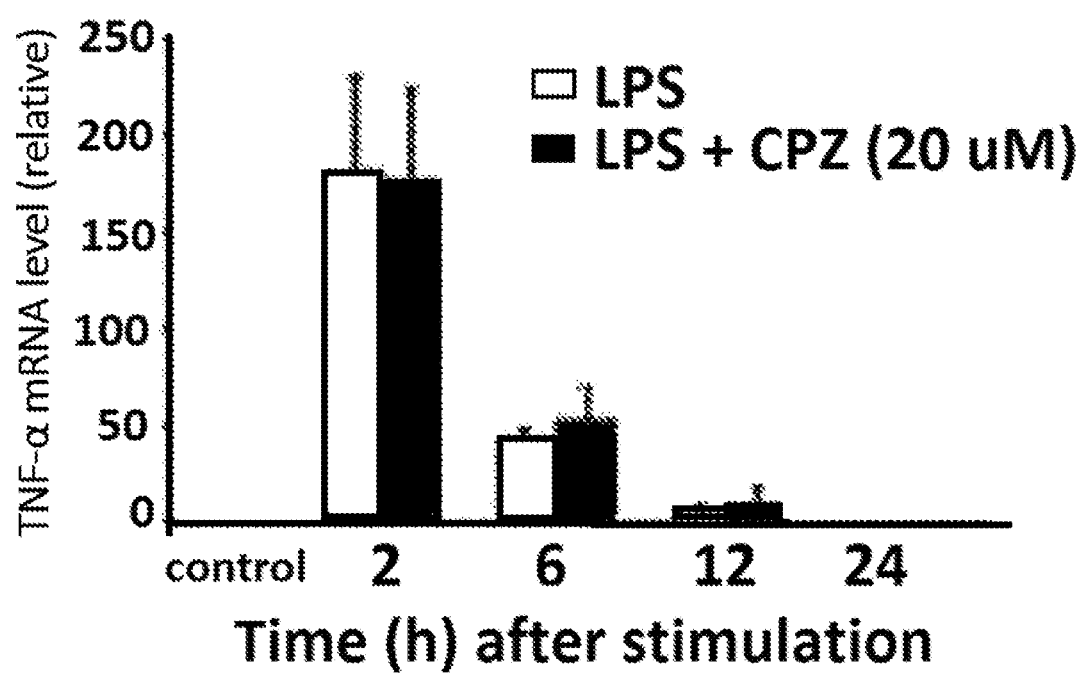
FIG. 11 is a graph showing mRNA expression of TNF-α in peritoneal macrophages.

A Method for Screening for a Candidate Substance Useful for the Treatment of a Lung Disease Peritoneal macrophages from C57BL/6 mice (aged 6 to 8 weeks) were stimulated with LPS (1 g/mL) in the presence or absence of a test agent (20 μM). The relative expression levels of mRNAs of Arid5A, IL-6, and TNF-α were determined in the stimulated peritoneal macrophages by quantitative PCR (qPCR). The expression level of Arid5A mRNA was determined 2 hours after LPS stimulation. The expression levels of IL-6 mRNA and TNF-α mRNA were determined 2 hours, 6 hours, 12 hours, and 24 hours after LPS stimulation. FIGS. 9 to 11 show the results when chlorpromazine (CPZ) was used as a test agent.

As shown in FIG. 9, the expression of Arid5A mRNA was markedly suppressed in the peritoneal macrophage stimulated with LPS in the presence of CPZ 2 hours after LPS stimulation as compared to the absence of CPZ. Also, as shown in FIG. 10, the expression of IL-6 mRNA was markedly suppressed in the peritoneal macrophage stimulated with LPS in the presence of CPZ 2 hours and 6 hours after LPS stimulation as compared to the absence of CPZ. In contrast, as shown in FIG. 11, CPZ had no effect on the expression of TNF-α mRNA.

The results revealed that CPZ was a substance that inhibits the expression itself of Arid5A mRNA. CPZ was also revealed to be a substance that inhibits the expression of IL-6 mRNA affected by Arid5A and has no effect on TNF-α mRNA known not to be affected by Arid5A. This suggests that CPZ is a substance that specifically inhibits stabilization of IL-6 mRNA and is effective in the treatment of lung diseases involved in inflammatory cytokines such as IL-6. Thus, it is expected that substances that are effective in the treatment of lung diseases can be obtained by screening for a substance that inhibits the expression of Arid5A mRNA within cells, and the substances that inhibit Arid5A action can be efficiently screened by screening for a substance that inhibits the expression of IL-6 mRNA and has no effect on TNF-α mRNA. These methods can be used to efficiently screen for a substance effective in the treatment of lung diseases.

INDUSTRIAL APPLICABILITY

The present invention provides pharmaceutical compositions having high therapeutic and/or prophylactic efficacy for a lung disease. The present invention also provides a method for screening for a therapeutic and/or prophylactic agent for a lung disease having high therapeutic efficacy.

The invention claimed is:

1. A method of treatment of at least one lung disease selected from pulmonary fibrosis and an inflammatory lung disease, comprising administering an effective amount of an Arid5A inhibitor to a subject having pulmonary fibrosis or an inflammatory lung disease.

2. The method according to claim 1, wherein the Arid5A inhibitor is at least one substance selected from the group consisting of a nucleic acid oligo and an Arid5A antibody.

3. The method according to claim 2, wherein the Arid5A inhibitor is a nucleic acid oligo consisting of a natural or non-natural RNA or DNA.

4. The method according to claim 1, wherein the lung disease is pulmonary fibrosis.

5. The method according to claim 2, wherein the lung disease is pulmonary fibrosis.

6. The method according to claim 3, wherein the lung disease is pulmonary fibrosis.

7. The method according to claim 1, wherein the lung disease is an inflammatory lung disease.

8. The method according to claim 2, wherein the lung disease is an inflammatory lung disease.

9. The method according to claim 3, wherein the lung disease is an inflammatory lung disease.

* * * * *

UNITED STATES PATENT AND TRADEMARK OFFICE
CERTIFICATE OF CORRECTION

| | |
|---|---|
| PATENT NO. | : 10,550,387 B2 |
| APPLICATION NO. | : 15/741224 |
| DATED | : February 4, 2020 |
| INVENTOR(S) | : Kishimoto et al. |

It is certified that error appears in the above-identified patent and that said Letters Patent is hereby corrected as shown below:

On the Title Page

Item (73), replace "Chugai Seiyaku Kabushiki Kaisha, Tokyo (JP)" with -- Chugai Seiyaku Kabushiki Kaisha, Tokyo (JP); Tadamitsu Kishimoto, Osaka (JP); Kazuya Masuda, Osaka (JP) --.

Signed and Sealed this
Seventh Day of February, 2023

Katherine Kelly Vidal
*Director of the United States Patent and Trademark Office*